(12) United States Patent
Coroneo (10) Patent No.: US 8,580,565 B2
(45) Date of Patent: *Nov. 12, 2013

(54) STEM CELL CULTIVATION DEVICES AND METHODS

(76) Inventor: Minas Theodore Coroneo, Sydney (AU)

(*) Notice: Subject to any disclaimer, the term of this patent is extended or adjusted under 35 U.S.C. 154(b) by 238 days.

This patent is subject to a terminal disclaimer.

(21) Appl. No.: 12/961,156

(22) Filed: Dec. 6, 2010

(65) Prior Publication Data

US 2011/0076320 A1     Mar. 31, 2011

Related U.S. Application Data

(63) Continuation of application No. 11/332,089, filed on Jan. 13, 2006, now Pat. No. 7,846,467.

(60) Provisional application No. 60/644,060, filed on Jan. 13, 2005.

(51) Int. Cl.
*C12N 5/00*     (2006.01)

(52) U.S. Cl.
USPC ........... 435/395; 424/427; 424/93.7; 604/521

(58) Field of Classification Search
None
See application file for complete search history.

(56) References Cited

U.S. PATENT DOCUMENTS

2005/0287223 A1    12/2005   Peyman

FOREIGN PATENT DOCUMENTS

WO    WO 02/053193 A2    7/2002

OTHER PUBLICATIONS

Ang, L.P. et al. 2004 "Ocular surface stem cells and disease: current concepts and clinical applications." *Ann Acad Med Singapore* 33:576-580.
Boulton, M. et al. 2004 "Stem cells in the eye." *Int J Biochem Cell Biol* 36:643-657.
Burman, S. et al. 2004 "Ophthalmic applications of preserved human amniotic membrane: a review of current indications." *Cell Tissue Bank* 5:161-75.
Daya, S.M. et al. 2005 "Outcomes and DNA analysis of ex vivo expanded stem cell allograft for ocular surface reconstruction." *Ophthalmology* 112:470-477.
Khor et al. 2003 "Preliminary study of polycaprolactone membrane utilized as epidermal substrate" *Journal of Materials Science: Materials in Medicine* 14:113-120.
Lavik, E.B. et al. 2005 "Fabrication of degradable polymer scaffolds to direct the integration and differentiation of retinal progenitors" *Biomaterials* 26:3187-3196.

*Primary Examiner* — Allison Ford
(74) *Attorney, Agent, or Firm* — Knobbe, Martens, Olson & Bear, LLP (57) ABSTRACT

The present invention relates to a device and methods for culturing stem cells, and in particular, for culturing ocular stem cells and the use of stem cells cultured using the devices and methods of the invention for the treatment of diseases.

29 Claims, 4 Drawing Sheets

STEM CELL CULTIVATION DEVICES AND METHODS

RELATED APPLICATIONS

This application is a continuation of U.S. application Ser. No. 11/332,089, filed Jan. 13, 2006, which claims the benefit of U.S. Provisional Application No. 60/644,060, filed Jan. 13, 2005, the entire disclosures of which are expressly incorporated herein by reference in their entireties.

FIELD OF THE INVENTION

The present invention relates to a device and methods for culturing stem cells, and in particular, for culturing ocular stem cells and the use of stem cells cultured using the devices and methods of the invention for the treatment of diseases.

DESCRIPTION OF THE RELATED ART

Stem cells are relatively undifferentiated cells that possess the ability to self-renew, and to generate one or more types of differentiated progeny or daughter cells, in adult or embryonic tissue.

Adult stem cells continually replace lost cells in healthy and damaged tissue types. There are a wide variety of different types of stem cells that are resident in the adult, human body, including in the brain, bone marrow, peripheral blood, blood vessels, skeletal muscle, eye, skin and liver.

A number of different stem-cell populations have been identified to date in the mammalian eye. Adult corneal and conjunctival stem cells are a small subpopulation of epithelial cells that make up the ocular surface, with corneal epithelial stem cells residing in the basal region of the limbus and playing a role in the regeneration of the corneal epithelium (Ang & Tan, 2004, Ann Acad Med Singapore, 33:576-80). Corneal stem cells, which are slow-cycling cells that self renew, mature to form transient, amplifying cells, which themselves give rise to progressively more differentiated, non-dividing cells of the anterior corneal epithelium (Boulton & Albon, Int Jour Biochem & Cell Biol, 2004, 36:643-657).

Conjunctival stem cells, which belong to a separate lineage from corneal stem cells, reside in the conjunctival forniceal region but can be found throughout other regions of the conjunctiva (Ang & Tan, above).

In three areas in particular, stem cell depletion has been recognized as underlying the etiology of eye disease. These three areas include:

1. The corneal-scleral limbus—a site of corneal epithelial stem cells;
2. The conjunctival fornices—a site of conjunctival epithelial stem cells; and
3. The retina/ciliary body junction—a site of retinal stem cells.

It is well recognized that the corneo-scleral limbus is important in regeneration of corneal epithelium and perhaps bulbar conjunctiva. The limbus is a specialized transitional zone where sclera (with overlying conjunctiva) merges with the cornea.

The superficial limbus is a narrow elliptical strip of tissue which extends circumferentially around the corneal periphery (where Bowman's membrane ends), the cornea having a superficial horizontal diameter of approximately 11.5 mm and a vertical diameter of 10.6 mm. In general terms, its posterior limit is a line running parallel to the corneal periphery, 2 mm beyond this limit vertically and 1.5 mm horizontally. Underling this, the flat curve of the sclera, meets the steeper curve of the cornea, resulting in a surface groove, the external scleral sulcus in which an implant could be placed without causing significant protrusion. Maintaining the "smoothness" of the ocular surface is important since "overhangs" can result in local drying of the surface of the eye which can cause devitalization of tissue (dellen) and even perforation of the eye.

The corneal epithelial stem cells are located in the palisades of Vogt, which are corregations that greatly increase limbal surface area and consequently, the number of cells present. The palisades are composed of epithelial rete pegs and the interpalisades are stromal papillae richly, vascularized (including lymphatics) and innervated.

The palisades of Vogt commence in the peripheral corneal epithelium and extend into the limbus as spoke-like radiations arranged at right angles to the peripheral cornea. The palisades measure 0.5 mm in width by 2-4 mm in length.

Other types of ocular stem cells that have been found in various anatomical locations in the eye include palpebral conjunctival epithelial stem cells, retinal stem cells and lens epithelial stem cells.

In relation to stem-cell related eye disease, stem cell depletion can occur in any of a number of stem cell populations, which usually occur in protected niches. Depletion of stem cells in these locations has serious consequences for eye health. Ocular stem cells are essentially pluri-potential but importantly, they are able to maintain tissue mass and normality of function by appropriated division and migrations as part of normal tissue turnover or in response to injury. Stem cells may also be critical to maintaining tissue borders, so that cell types do not overgrow boundaries. This is critical in maintaining the precise optical functions of the eye.

Ocular disorders that are a result of deficiencies include hereditary and acquired diseases or conditions, including aniridia keratitis and keratitis caused by endocrine deficiency, Steven-Johnson syndrome, ocular cicatricial pemphigoid, contact lens-induced keratopathy, neurotrophic keratopathy and peripheral ulcerative keratitis.

To date, the treatment of ocular stem cell deficiencies has included grafting tissue from a patient's healthy eye into the diseased eye. For example, in limbal stem cell deficiency, a lamellar removal of limbal segments from a patient's healthy eye can be transplanted to the limbal-deficient eye, following a complete, superficial keratectomy and conjunctival peritomy for removal of diseased surface epithelium in the affected eye (Ang & Tan, above). However, the use of autologous stem cells is not possible where a patient has bilateral stem cell deficiency, necessitating the use of allogenic stem cells, which can be associated with a graft-rejection response. Immunosuppressant medications can be administered to minimize the risk of such a response (Boulton & Albon, above), however, such drugs are not without substantial side effects.

More recently, ex vivo expansion of ocular stem cells has been attempted, where a small biopsy from the patient's eye provides a small population of the appropriate stem cell type, which is then cultured on planar substrates, such as human amniotic membranes or fibrin-based substrates (see e.g. Burman et al., Cell Tissue Bank. 2004; 5(3):161-75). In a study of the use of cells derived in this manner, however, ex vivo, allograft limbal stem cells that were used to treat limbal stem cell deficient patients were found to have a considerably short lifetime in the eye. In particular, PCR analysis showed no donor DNA present just three months after the procedure was performed (Daya, American Academy of Ophthalmology Annual Meeting, 2003, Abstract).

A number of diseases and conditions have been, and may potentially be, treated or prevented using stem-cell therapy, that is, the replacement of a patient's damaged or abnormal stem cells with healthy populations of stem cells, or the implantation of replacement cell types, that have been derived (differentiated) from stem cells, to replace differentiated cells that have been damaged by disease or other trauma. For example, the growth and differentiation of dopaminergic neural cells from neural stem cells has been proposed as a means of replacing damaged dopamine-producing neurons in Parkinson's disease, as has the replacement of insulin-producing pancreatic cells in type-1 diabetes from multipotent pancreatic stem cells. Other conditions that may benefit from stem cell supplementation, or replacement of diseased or damaged differentiated cells with differentiated, stem-cell progeny include spinal cord injuries, incontinence, cardiovascular diseases, burns, arthritis and various liver and kidney diseases.

Adult stem cells are usually grown in culture dishes in incubators at body temperature (i.e. 37° C.), under conditions of high humidity and with nutrients that are specific for a given stem-cell type. A commonly encountered difficulty is obtaining adequate numbers of stem cells in an undifferentiated state. This is because adult stem cells are very difficult to isolate and culture as they are few in number (e.g. only 1 in 10 billion bone marrow cells are stem cells), and the cells have a tendency to stop dividing in culture after a time. They also tend to lose their ability to differentiate when they are grown in culture, and it can thus be difficult to promote the differentiation of the cells when the need arises.

Given the potential of stem cells and their differentiated progeny for therapeutic purposes, there is thus a need for improved techniques for stem-cell proliferation.

SUMMARY OF THE INVENTION

The present invention is based on the finding that stem cell proliferation can be promoted by providing the cells with a specific micro-environment, which encourages proliferation and/or differentiation of stem cells.

Accordingly, in a first broad form, the present invention relates to a method for promoting stem cell proliferation and/or differentiation comprising seeding stem cells into a scaffold device comprising an internal compartment having a plurality of folds, and providing the internal compartment with an appropriate nutrient supply capable of inducing proliferation and/or differentiation of the stem cells.

In one preferred form, the stem cell proliferation and/or differentiation is performed in vitro.

In a further preferred form, the stem cell proliferation and/or differentiation is performed in vivo.

In another preferred form, the scaffold device is shaped on an external and/or internal surface to mimic an anatomical environment.

In one embodiment, the anatomical environment is a source of the stem cells.

In another embodiment, the anatomical environment is the desired transplantation site of the stem cells and/or their differentiated progeny.

In a preferred form, the stem cells are ocular stem cells.

Preferably, the ocular stem cells are limbal stem cells.

In a further preferred form, the ocular stem cells are conjunctival epithelial stem cells.

In yet another preferred form, the ocular stem cells are retinal progenitor cells.

In a further preferred form, the ocular stem cells are corneal epithelial stem cells.

In yet a further preferred form, the ocular stem cells are palpebral conjunctival epithelial stem cells.

In another preferred form, the ocular stem cells are epithelial stem cells.

Preferably, the scaffold device further comprises an external surface having a plurality of external folds.

In a preferred form, the external surface and external folds promote neovascularisation.

Preferably, neovascularisation occurs prior to seeding the stem cells in the scaffold device.

In a particularly preferred form, the scaffold device is implanted in a patient's eye.

In yet another preferred form, the scaffold device is implanted under a patient's limbus.

In a one embodiment, the scaffold device is an oval shaped scaffold device.

Preferably, the oval shaped scaffold device has a vertical diameter of between about 8 mm and 12 mm, a horizontal diameter of between about 9 mm and 14 mm, and a width of about 0.5 mm to 4 mm.

In another preferred form, the plurality of folds of the internal compartment of the scaffold device increase an internal surface area of the scaffold device by two orders of magnitude.

In this preferred form, the plurality of folds have dimensions of about 30-50 microns in width and the length of about 36-90 microns, and an interfold spacing of about 70-150 microns.

Preferably, the scaffold device is implanted at the fornices of the conjunctiva.

In another preferred form, the scaffold device is implanted at a lid margin.

In yet another preferred form, the scaffold device is a rod-shaped scaffold device.

Preferably, the rod-shaped scaffold device has a diameter of about 0.2 to 3 mm and a length of about 20-50 mm.

Even more preferably, in this embodiment, the scaffold device is implanted at the patient's mucocutaneous junction.

In another preferred form according to this embodiment, the scaffold device is implanted at the patient's ciliary margin, between the patient's retina and ciliary body.

Preferably, the stem cells that are seeded in the scaffold devices of the invention are autologous stem cells.

In another preferred form, the stem cells that are seeded in the scaffold devices of the invention are allogenic stem cells.

Preferably, the scaffold device is made of a biocompatible material.

Even more preferably, the biocompatible material is bioabsorbable.

In a further preferred form, the biocompatible material is poly(e-caprolactone).

In yet another preferred form, the biocompatible material is a biosynthetic hybrid scaffold comprised of a fibrinogen backbone and crosslinked with difunctional polyethylene glycol side chains.

In another broad form, the present invention provides a scaffold device for promoting stem cell proliferation and/or differentiation comprising an internal compartment having a plurality of folds.

Preferably, the scaffold device is shaped on an external and/or internal surface to mimic an anatomical environment.

In a preferred form, the anatomical environment is a source of the stem cells.

In another preferred form, the anatomical environment is the desired transplantation site of the stem cells and/or their differentiated progeny.

Preferably, the scaffold device of the invention further comprises an external surface having a plurality of external folds.

In one preferred form, the plurality of external folds promotes neovascularisation.

In a further preferred form, the scaffold device is an oval shaped scaffold device.

Preferably, the oval shaped scaffold device has a vertical diameter of between about 8 mm and 12 mm, a horizontal diameter of between about 9 mm and 14 mm, and a width of about 0.5 mm to 4 mm.

In a particularly preferred form, the plurality of folds of the internal compartment of the scaffold device increase an internal surface area of the scaffold device by two orders of magnitude.

In a preferred form, the plurality of folds have dimensions of about 30-50 microns in width and the length of about 36-90 microns, and an interfold spacing of about 70-150 microns.

In a further preferred form, the scaffold device is a rod-shaped scaffold device.

Preferably, the rod-shaped scaffold device has a diameter of about 0.2 to 3 mm and a length of about 20-50 mm.

In a particularly preferred form, the scaffold device of the invention is made of a biocompatible material.

Preferably, the biocompatible material is bio-absorbable.

In another preferred form, the biocompatible material is poly(e-caprolactone).

In a further preferred form, the biocompatible material is a biosynthetic hybrid scaffold comprised of a fibrinogen backbone and crosslinked with difunctional polyethylene glycol side chains.

In another broad form, the present invention relates to an ocular scaffold device for promoting ocular stem cell proliferation and/or differentiation comprising an internal compartment having a plurality of internal folds and an external surface comprising a plurality of external folds for promoting neovascularisation, the internal compartment for seeding with stem cells, the ocular scaffold device being made from poly(e-caprolactone).

Preferably, the ocular scaffold device is implantable into an eye of a patient.

In a further form, the present invention relates to a method of treating or preventing a disease in a patient comprising administering to the patient stem cells and/or their differentiated progeny, obtained according to any of the methods of the invention.

In yet another form, the invention relates to a method of treating or preventing a disease in a patient comprising in vivo growth in the patient of stem cells and/or their differentiated progeny, according to any of the methods for in vivo stem cell proliferation of the invention.

In a further form, the present invention relates to a method of treating or preventing a disease in a patient comprising implantation into the patient of a scaffold device for promoting in vivo stem cell proliferation and/or differentiation in the patient.

DETAILED DESCRIPTION OF THE PREFERRED EMBODIMENT

Throughout this specification, unless the context requires otherwise, the words "comprise," "comprises" and "comprising" will be understood to imply the inclusion of a stated step or element or group of steps or elements but not the exclusion of any other step or element or group of steps or elements.

In a first broad form, the present invention relates to a scaffold device having an internal compartment with plurality of internal folds, which can be seeded with stem cells, and to methods of proliferating and/or differentiating stem cells using the scaffold device. The internal folds of the scaffold device provide an increased surface area for supporting the stem cells that are seeded into the scaffold device for proliferation and/or differentiation.

The internal compartment is provided with an adequate nutrient supply capable of inducing proliferation and/or differentiation of the stem cells therein. For example, the nutrient supply may be provided by fashioning holes and/or tubing in an external surface of the scaffold device, the holes permitting the flow of cell culture broth or blood through to the internal compartment of the device. Alternatively, the nutrient supply may be injected into the internal compartment.

In a preferred form, the scaffold device has an external surface having a number of external infoldings, which permit neovascularisation of the scaffold device, thus also providing a nutrient supply to the internal compartment of the scaffold device.

Preferably, the scaffold device may be used in vivo or in vitro for the proliferation of stem cells.

Preferably, stem cells that are seeded in the scaffold device are autologous stem cells. Sources of autologous stem cells include multipotent adult progenitor stem cells, also known as MAPCs, isolated from bone marrow or other tissues in which they reside, mesenchymal stem cells derived from bone marrow, chord blood-derived stem cells, chord matrix (Wharton's jelly)-derived stem cells, and tissue-specific stem cells, for example, ocular stem cells.

In one embodiment, the scaffold device is shaped on its external and/or internal surface to mimic an anatomical environment, which may be an anatomical environment that the stem cells being grown in the device are isolated from. For example, the internal surface of the scaffold device, which has a plurality of folds in its internal compartment, may mimic spongy bone, which consists of trabeculae and bars of bone adjacent to small, irregular cavities that contain red bone marrow. A further example is where the foldings of the internal compartment of the scaffold device may mimic the shape of liver lobules, and thus promote the proliferation and/or differentiation of stem cells into hepatic stem cells or hepatocytes.

Alternatively, the anatomical environment is a site where the stem cells and/or their differentiated progeny will be transplanted in a patient. For example, it is known that stem cells from adult brain when transplanted into sublethally irradiated mice will colonize the host bone marrow and differentiate into granulocytes, macrophages, and B cells. Accordingly, stem cells from one tissue may be placed in a scaffold device that is shaped on its external and/or internal surface to mimic the new anatomical microenvironment and thus encourage the proliferation and differentiation of stem cells derived from a different tissue. The shape of the scaffold structure can thus exploit the pluripotent nature of a variety of stem cells.

The term "patient" refers to patients of human or other mammal and includes any individual it is desired to examine or treat using the methods and devices of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

Preferably, the patient is human.

In a preferred embodiment, the scaffold device is implantable in a patient.

In a particularly preferred form, the implantable device mimics the anatomy of the ocular stem cell niches of a patient in areas including, but not restricted to, the three areas of corneal and conjunctival epithelial as well as retinal stem cells.

In this form, the ocular scaffold device will conform to the normal anatomy of the three areas, where the foldings of the internal compartment, greatly increase tissue surface area.

Figure 1:
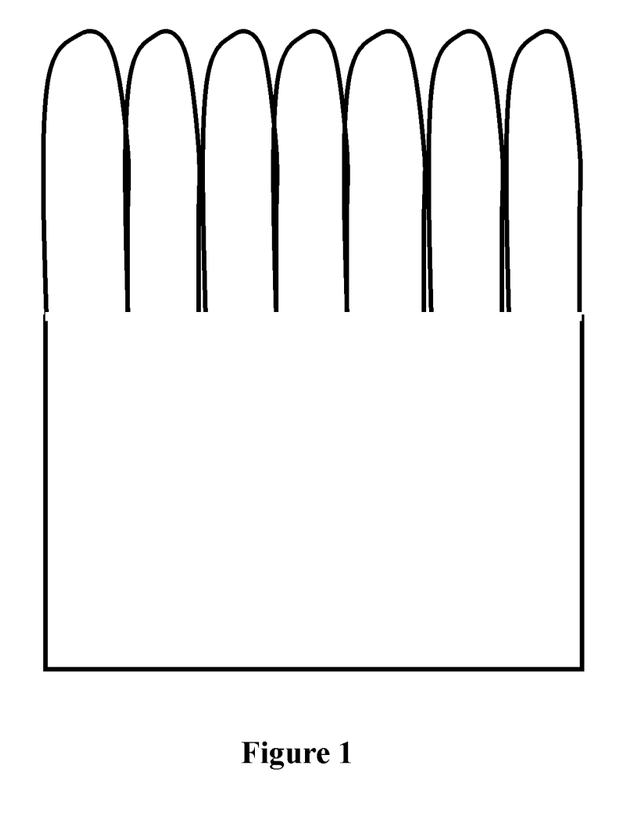
FIG. 1 is a diagramatic side view of an example of an ocular scaffold device.

In this embodiment, the ocular scaffold device thus has two compartments: an external compartment and an internal compartment. The external compartment comprises a surface that has a plurality of external foldings, which, after implantation is invaded by blood vessels. After this has occurred an internal compartment and its foldings will be populated by cultured stem cells, which can be injected into the internal compartment by a few openings to the exterior. An example of an ocular scaffold device according to this embodiment is shown in FIG. 1, which shows an external schematic view of an example of an ocular implantable scaffold device of the invention. The complex inner foldings of the internal compartment are not shown in this representation.

Preferably, the scaffold devices of the invention are manufactured from material that is chosen so that it minimizes the risk of causing an inflammatory or toxic response. Suitable scaffold materials include, but are not limited to, type I collagen; glycosaminoglycans such as hyaluronic acid, dermatan sulphate, chondroitin sulphate, heparin, heparan sulphate, and keratan sulphate; chitosan; polyhydroxyalkanoates polyesters; poly-caprolactone and poly (glycolic acid, poly (lactic acid) and their copolymers.

In a particularly preferred form, the scaffold material is poly(e-caprolactone), or a biosynthetic hybrid scaffold comprised of a fibrinogen backbone and crosslinked with difunctional polyethylene glycol side chains.

In one embodiment, the scaffold device is manufactured from a material that is bio-absorbable, that is, it is metabolized in the body after fulfilling its purpose, leaving substantially no trace.

Preferably, the rate of matrix regeneration is close to the biodegradability rate of the scaffold.

In a further broad form, the present invention relates to methods of treating or preventing a disease or condition in a patient comprising administering to the patient stem cells obtained according to any of the methods of the invention, or in vivo growth in the patient of stem cells according to any of the methods of the invention for in vivo stem cell proliferation and/or differentiation.

In another form, the present invention relates to a method of treating or preventing a disease or condition in a patient comprising implantation into the patient of a scaffold device for promoting in vivo stem cell proliferation and/or differentiation in the patient.

The terms "disease" and "condition" as used herein are interchangeable, and refer to an impairment of health or a state of health characterized by abnormal functioning in a patient.

Diseases that may be treated according to the methods of the invention include, but are not limited to, Parkinson's disease, Alzheimer's disease, spinal cord injury, stroke, burns, cancer, incontinence, heart disease, certain inherited blood disorders, type 1 diabetes, osteoarthritis, rheumatoid arthritis, muscular dystrophies, liver diseases, alopecia, certain liver and kidney disorders, and ocular diseases.

In relation to a number of ocular diseases and conditions, it is now recognized that a primary cause is the depletion of stem cell populations, resulting in failure to maintain the normal features of that tissue. This can be the result of trauma, such as chemical injury to the surface of the eye. It may also be that stem cell depletion is part of the aging process. Inability to maintain normal tissue characteristics impacts on vision, typically because transparency of tissue is affected, causing image degradation.

Figure 2:
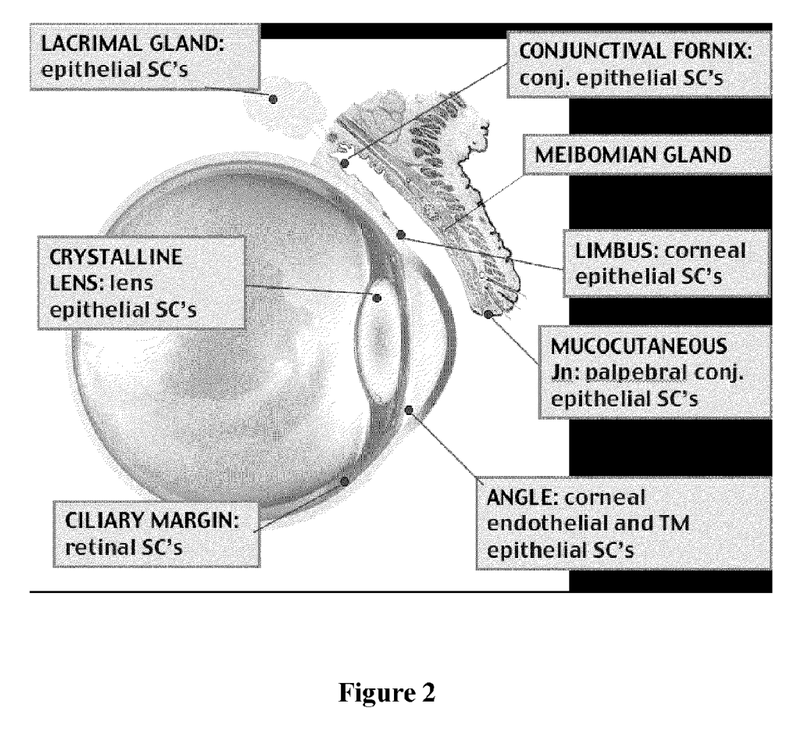
FIG. 2 is a schematic representation of a mammalian eye showing the location of ocular stem cell populations.

Certain ocular stem cell populations are shown in FIG. 2. In most instances, the stem cells are located in relatively protected niches and usually the tissue in these areas are thrown into folds, greatly increasing tissue surface area and consequently the number of cells that can be located there. This may be critical given the limited space in and on the eye.

Figure 3:
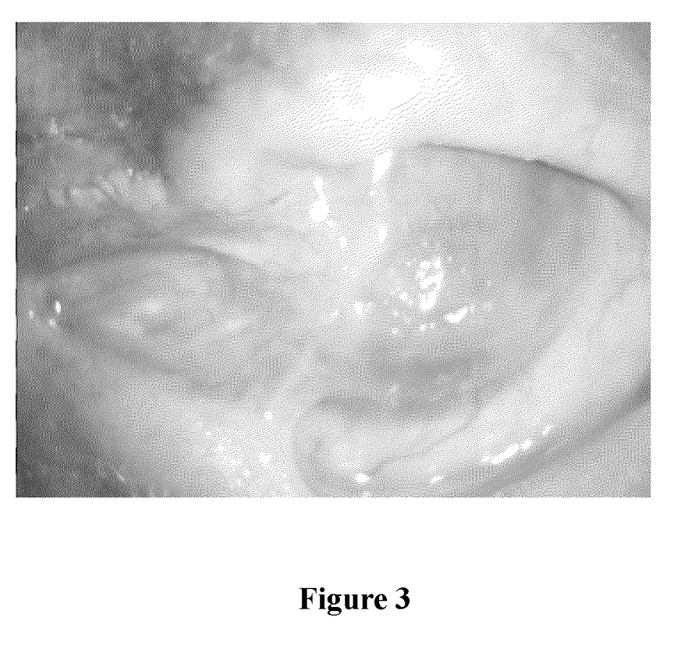
FIG. 3 is an illustration of injury to an eye of a patient caused by chemical insult.
Figure 4:
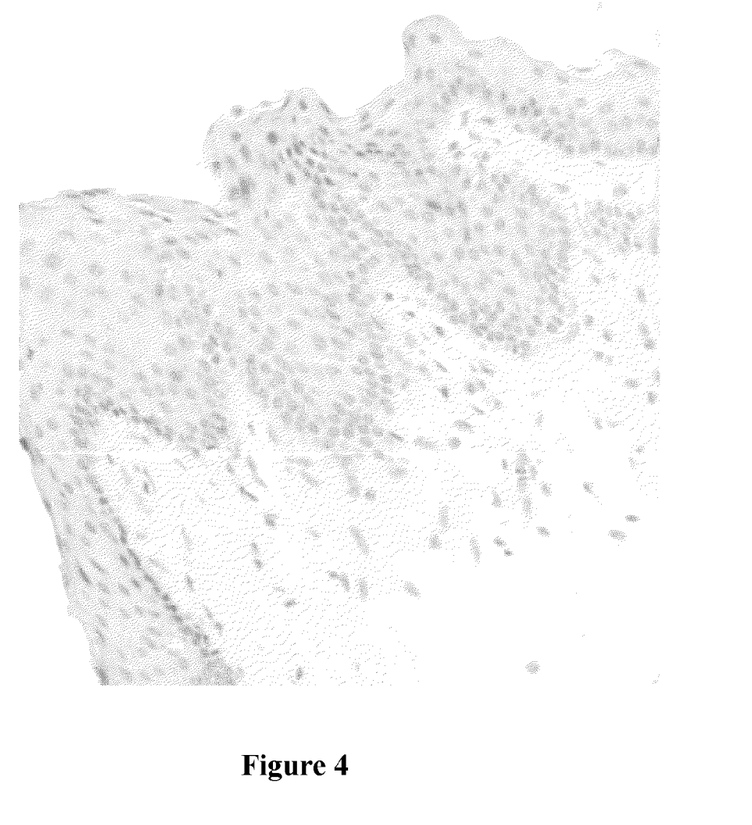
FIG. 4 is an illustration showing normal Palisades of Vogt of the limbus.

An example of chemical injury causing corneal and conjunctival stem cell depletion is shown in FIG. 3. FIG. 3 demonstrates corneal opacity, conjunctival scarring and lack of eyelashes and a well-defined, eyelid margin as a result of deficiencies in corneal and conjunctival stem cell populations caused by chemical injury, which has depleted stem cell populations including those of the limbus. As part of limbal stem cell failure, the infoldings of the limbus (Palisades of Vogt, see FIG. 4) are lost and these infoldings greatly increase tissue surface area and therefore cell numbers.

Without being limited to any single theory or mode of action, it is postulated that stem cells, when placed in culture or following attempts to replace a patient's own stem cell populations, suffer a loss of "sternness", which may, in part, be caused by a failure to recreate a "niche" or an appropriate, pseudo-anatomical environment that protects and promotes proliferation of stem cells. In the absence of such an environment, stem cells will not survive in sufficient numbers of cells present to last long term, particularly when placed in the body of a patient, or will not differentiate sufficiently or appropriately.

In order that the invention may be readily understood and put into practical effect, particular preferred embodiments will now be described by way of the following non-limiting examples.

Persons skilled in the art will appreciate that numerous variations and modifications will become apparent. All such variations and modifications which become apparent to persons skilled in the art, should be considered to fall within the spirit and scope that the invention broadly appearing before described.

Example 1

Limbal Stem Cell Scaffold Device

This scaffold device is designed to conform to standard limbal dimensions and is oval in shape—(normal corneal dimensions: vertical diameter: 10.6 mm, horizontal diameter: 11.75 mm) with a width of 1-2 mm.

The ocular scaffold devices consist of a biocompatible polymer scaffold which will, after the vascular and stem cell components are established will dissolve. This substance, in the first instance is poly(e-caprolactone) or a biosynthetic hybrid scaffold comprised of a fibrinogen backbone and crosslinked with difunctional polyethylene glycol (PEG) side chains. In this regard, it has recently been demonstrated that autologous human conjunctival epithelial stem cells can be grown on polycaprolactone and successfully transplanted back onto deficient human ocular surfaces.

The under surface (that surface which lies on the globe at the limbus is infolded) and the external surface, smooth. Internally the structure is infolded to mimic the normal limbal anatomy, so that the surface area is increased by approximately 2 orders of magnitude. The normal limbal palisades of Vogt are 30-50 microns wide, the interpalisade width is 70-150 microns and the length of each palisade, 36-90 microns.

This internal cavity is sealed but is accessible after implantation (after the basal surface of the implant is vascularized). Corneal epithelial stem cells are then injected into this cavity and after they have colonized the scaffold device, the scaffold dissolves, leaving behind a new "pseudo-limbus" that mimics the original.

The implantation procedure is carried out under local anaesthetic. The conjunctiva is detached from the limbus (i.e. peritomy), and the implant laid on the limbal "groove" (i.e. the external scleral sulcus, where the disparate curvatures of the cornea and sclera meet). The implant can be secured in place with an absorbable suture such as 10-0 Biosorb (polyglycolic acid) and the conjunctiva is closed over the implant with the same suture material.

Example 2

Conjunctival Epithelial Stem Cell Scaffold Device

Conjunctival epithelial stem cell populations exist in the conjunctival fornices, the mucocutaneous junction of the eyelid and perhaps in the limbus. The device for implantation in this context is ideally rodlike for insertion in the fornix and/or lid margin. The implants are thus rod like and of 0.5 to 2 mm diameter and 30-40 mm in length. For the fornices (superior and inferior), small incisions are made in the conjunctiva laterally. By using a blunt probe, a space is opened along the length of each fornix and the implant inserted. Similarly, for the eyelid margins, a small incision is made laterally and a blunt probed used to open a passage the length of the eyelid margin.

Example 3

Retinal Stem Cell Scaffold Device

Retinal stem cells have been identified at the junction of the ciliary body and peripheral retina. This region is relatively thin and importantly avascular. The region is 6-9 mm posterior to the limbus and has a diameter of 10-24 mm. Using standard vitrectomy/retinal surgery techniques, instruments are inserted into the eye, and this junctional zone identified and incised. A probe is then inserted and a subretinal space created into which the implant is inserted.

What is claimed is:

1. A method for promoting stem cell proliferation and/or differentiation comprising seeding stem cells into a scaffold device comprising an internal compartment having a plurality of micron-sized internal folds configured to create niches for proliferation of the stem cells, and providing the internal compartment with an appropriate nutrient supply capable of inducing proliferation and/or differentiation of the stem cells in the niches, wherein the plurality of micron-sized internal folds increase an internal surface area of the scaffold device by at least two orders of magnitude compared to the surface area of the internal compartment without folds.

2. The method according to claim 1, wherein the plurality of folds have dimensions of about 30-50 microns in width and the length of about 36-90 microns, and an interfold spacing of about 70-150 microns.

3. The method according to claim 1, wherein the stem cell proliferation and/or differentiation occurs in vitro.

4. The method according to claim 1, wherein the stem cell proliferation and/or differentiation occurs in vivo.

5. The method according to claim 1, wherein the scaffold device is shaped on an external and/or internal surface to mimic an anatomical environment.

6. The method according to claim 5, wherein the anatomical environment is a source of the stem cells.

7. The method according to claim 5, wherein the anatomical environment is the desired transplantation site of the stem cells and/or their differentiated progeny.

8. The method according to claim 1, wherein the stem cells are ocular stem cells.

9. The method according to claim 8, wherein the ocular stem cells are selected from the group consisting of limbal stem cells, conjunctival epithelial stem cells, retinal progenitor cells, corneal epithelial stem cells and palpebral conjunctival epithelial stem cells.

10. The method according to claim 1, wherein the scaffold device further comprises an external surface having a plurality of external folds.

11. The method according to claim 10, wherein the external surface and external folds promote neovascularisation.

12. The method according to claim 11, wherein neovascularisation occurs prior to seeding the stem cells in the scaffold device.

13. The method according to claim 1, further comprising implanting the scaffold device into a patient's eye.

14. The method according to claim 1, further comprising implanting the scaffold device under a patient's limbus.

15. The method according to claim 1, wherein the scaffold device is an oval shaped scaffold device.

16. The method according to claim 15, wherein the oval shaped scaffold device has a vertical diameter of between about 8 mm and 12 mm, a horizontal diameter of between about 9 mm and 14 mm, and a width of about 0.5 mm to 4 mm.

17. The method according to claim 16, further comprising implanting the scaffold device at the fornices of the conjunctiva.

18. The method according to claim 16, further comprising implanting the scaffold device at a lid margin.

19. The method according to claim 1, wherein, the scaffold device is a rod-shaped scaffold device.

20. The method according to claim 19, wherein the rod-shaped scaffold device has a diameter of about 0.2 to 3 mm and a length of about 20-50 mm.

21. The method according to claim 20, further comprising implanting the scaffold device at a patient's mucocutaneous junction.

22. The method according to claim 20, further comprising implanting the scaffold device at a patient's ciliary margin, between the patient's retina and ciliary body.

23. The method according to claim 13, wherein the stem cells that are seeded in the scaffold devices of the invention are autologous to the patient.

24. The method according to claim 13, wherein the stem cells that are seeded in the scaffold devices of the invention are allogeneic to the patient.

25. The method according to claim 1, wherein the scaffold device is made of a biocompatible material.

26. The method according to claim 25, wherein the biocompatible material is bio-absorbable.

27. The method according to claim 26, wherein the biocompatible material is poly(e-caprolactone).

28. The method according to claim 26, wherein the biocompatible material is a biosynthetic hybrid scaffold comprised of a fibrinogen backbone and crosslinked with difunctional polyethylene glycol side chains.

29. A method of treating or preventing a disease in a patient comprising in vivo growth in the patient of stem cells and/or their differentiated progeny, according to the method of claim 4.

\* \* \* \* \*